United States Patent
Kuzma et al.

(10) Patent No.: US 7,444,180 B2
(45) Date of Patent: Oct. 28, 2008

(54) IMPLANTABLE MICROSTIMULATOR WITH DISSECTING TIP AND/OR RETRIEVING ANCHOR AND METHODS OF MANUFACTURE AND USE

(75) Inventors: Janusz A. Kuzma, Parker, CO (US); Tom Xiaohai He, Simi Valley, CA (US); Anne Pianca, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 177 days.

(21) Appl. No.: 11/138,598

(22) Filed: May 25, 2005

(65) Prior Publication Data
US 2006/0271109 A1 Nov. 30, 2006

(51) Int. Cl.
*A61N 1/00* (2006.01)

(52) U.S. Cl. .......................................................... 607/2

(58) Field of Classification Search ................ 607/2, 607/61; 606/129, 41, 190, 191
See application file for complete search history.

(56) References Cited

U.S. PATENT DOCUMENTS

| | | | | |
|---|---|---|---|---|
| 4,333,469 A | * | 6/1982 | Jeffcoat et al. | 607/5 |
| 4,913,164 A | * | 4/1990 | Greene et al. | 607/126 |
| 5,170,801 A | * | 12/1992 | Casper et al. | 600/582 |
| 5,193,539 A | | 3/1993 | Schulman | |
| 5,193,540 A | * | 3/1993 | Schulman et al. | 607/61 |
| 5,211,175 A | * | 5/1993 | Gleason et al. | 600/548 |
| 5,312,439 A | | 5/1994 | Loeb | |
| 5,405,367 A | * | 4/1995 | Schulman et al. | 607/61 |
| 5,871,509 A | * | 2/1999 | Noren | 607/9 |
| 5,999,848 A | * | 12/1999 | Gord et al. | 607/2 |
| 6,051,017 A | | 4/2000 | Loeb | |
| 6,185,452 B1 | * | 2/2001 | Schulman et al. | 604/20 |
| 6,609,032 B1 | | 8/2003 | Woods | |
| 6,941,171 B2 | * | 9/2005 | Mann et al. | 607/39 |
| 7,079,881 B2 | * | 7/2006 | Schulman et al. | 600/347 |
| 2003/0078618 A1 | * | 4/2003 | Fey et al. | 607/2 |
| 2004/0059392 A1 | | 3/2004 | Parramon | |
| 2004/0064024 A1 | * | 4/2004 | Sommer | 600/374 |

FOREIGN PATENT DOCUMENTS

| | | |
|---|---|---|
| WO | WO 98/37926 | 9/1998 |
| WO | WO 98/43700 | 10/1998 |
| WO | WO 98/43701 | 10/1998 |

OTHER PUBLICATIONS

U.S. Appl. No. 11/040,209, filed Jan. 20, 2005, Colvin et al.
U.S. Appl. No. 11/056,762, filed Feb. 11, 2005, Tom Xiaohai He.

* cited by examiner

*Primary Examiner*—Carl H. Layno
*Assistant Examiner*—Jon-Eric C. Morales
(74) *Attorney, Agent, or Firm*—Fish & Richardson P.C.

(57) ABSTRACT

An implantable microstimulator can include a housing having a first end; an electronic subassembly disposed within the housing; a plurality of electrodes disposed on the housing and coupled to the electronic subassembly; and a dissecting tip disposed at the first end of the housing. Another implantable microstimulator includes a housing having a first end; an electronic subassembly disposed within the housing; a plurality of electrodes disposed on the housing and coupled to the electronic subassembly; and a extraction aid disposed at the first end of the housing and configured and arranged for attachment of an extraction line.

25 Claims, 4 Drawing Sheets

US 7,444,180 B2

IMPLANTABLE MICROSTIMULATOR WITH DISSECTING TIP AND/OR RETRIEVING ANCHOR AND METHODS OF MANUFACTURE AND USE

FIELD

The invention is directed to implantable microstimulators with a dissecting tip, such as a blunt dissecting tip, and methods of manufacturing and using the devices. In addition, the invention is directed to implantable microstimulators with an extraction aid to assist in extracting an implanted microstimulator using an extraction line and methods of manufacturing and using the devices.

BACKGROUND

Implantable microstimulators have been developed to provide therapy for a variety of disorders, as well as to provide other treatments. For example, implantable microstimulators can be used in neurological therapy by stimulating nerves or muscles, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc.

Implantable microstimulators, such as the BION® device (available from Advanced Bionics Corporation, Sylmar, Calif.), have exposed electrodes and a small, often cylindrical, housing that contains the electronic circuitry and power source that produce electrical pulses at the electrodes for stimulation of the neighboring tissue. It is preferable that the electronic circuitry and power source be held within the housing in a hermetically-sealed environment for the protection of the user and the protection of the circuitry and power source. Once implanted, it is often preferable that the microstimulator can be controlled and/or that the electrical source can be charged without removing the microstimulator from the implanted environment.

These cylindrical devices are typically implanted using a surgical tool that includes a blunt dissector. An insertion passage inside the human body is created using the blunt dissector. The dissector may be connected to an external electrical pulse generator to assist in identifying the location of the target tissue. To implant the microstimulator, the blunt dissector tool must be withdrawn and the microstimulator inserted through the passage created by the tool. It can be difficult, however, to maintain the position of the tool during the exchange of the dissector and the microstimulator. During this exchange, the exact location of the target tissue, such as a nerve, can be lost and then the process must be repeated using the dissector.

Furthermore, the small size of the microstimulator can make it difficult to extract the implanted microstimulator from the human body, when desired (for example, when the battery is no longer usable or when there is no further need for the device.) Typically, a cut-down procedure or a large diameter tool is used to locate the microstimulator and remove it from the tissue. This can be damaging to the tissue and its surroundings.

BRIEF SUMMARY

One embodiment is an implantable microstimulator including a housing having a first end; an electronic subassembly disposed within the housing; a plurality of electrodes disposed on the housing and coupled to the electronic subassembly; and a dissecting tip disposed at the first end of the housing.

Another embodiment is an implantable microstimulator including a housing having a first end; an electronic subassembly disposed within the housing; a plurality of electrodes disposed on the housing and coupled to the electronic subassembly; and an extraction aid disposed at the first end of the housing and configured and arranged for attachment of an extraction line.

Yet another embodiment is a method of using an implantable microstimulator having a housing having a first end, an electronic subassembly disposed within the housing, a plurality of electrodes disposed on the housing and coupled to the electronic subassembly, and a dissecting tip disposed at the first end of the housing. The microstimulator is inserted in a body of a patient using the dissecting tip to open a path to body tissue to be stimulated. Signals are then provided to the electrodes to stimulate the body tissue.

A further embodiment is a method of using an implantable microstimulator having a housing having a first end, an electronic subassembly disposed within the housing, a plurality of electrodes disposed on the housing and coupled to the electronic subassembly, and an extraction aid disposed at the first end of the housing and configured and arranged for attachment of an extraction line. The microstimulator is inserted in a body of a patient. Signals are then provided to the electrodes to stimulate the body tissue. The implantable microstimulator can be removed from the body using the extraction aid.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to implantable microstimulators with a dissecting tip, such as a blunt dissecting tip, and methods of manufacturing and using the devices. In addition, the present invention is directed to implantable microstimulators with an extraction aid to assist in extracting an implanted microstimulator using an extraction line and methods of manufacturing and using the devices.

Microstimulators have been developed for stimulating tissue such as, for example, nerves, muscles, and organ tissues. Examples of such microstimulators are found in U.S. Pat. Nos. 5,193,539; 5,193,540; 5,312,439; 6,051,017; and 6,609,032; U.S. Patent Application Publication No. 2004/059392; U.S. patent applications Ser. Nos. 11/040,209 and 11/056, 762; and PCT Patent Applications Publication Nos. 98/37926; 98/43700; and 98/43701, all of which are incorporated herein by reference.

An implantable microstimulator can be formed with a dissecting tip, preferably, a blunt dissecting tip, at one end. This configuration allows the implantable microstimulator to be directly implanted using the dissecting tip to form the opening through the body tissue to the desired implantation site. In some embodiments, the dissecting tip can be used as an electrode for the microstimulator and may also be useful for finding and detecting the tissue to be stimulated as the microstimulator is implanted.

An implantable microstimulator can be formed with an extraction aid at one end to aid in extracting or explanting the device from the tissue. For example, a practitioner can couple an extraction line to the extraction aid during or prior to implantation. When extraction is performed, the practitioner can use the extraction line to locate and retrieve the attached microstimulator. Optionally, an anchor can be attached to the opposite end of the extraction line and implanted, for example, near the skin of the patient. The anchor may be relatively easy to identify using x-ray or other detection methods.

Figure 1:
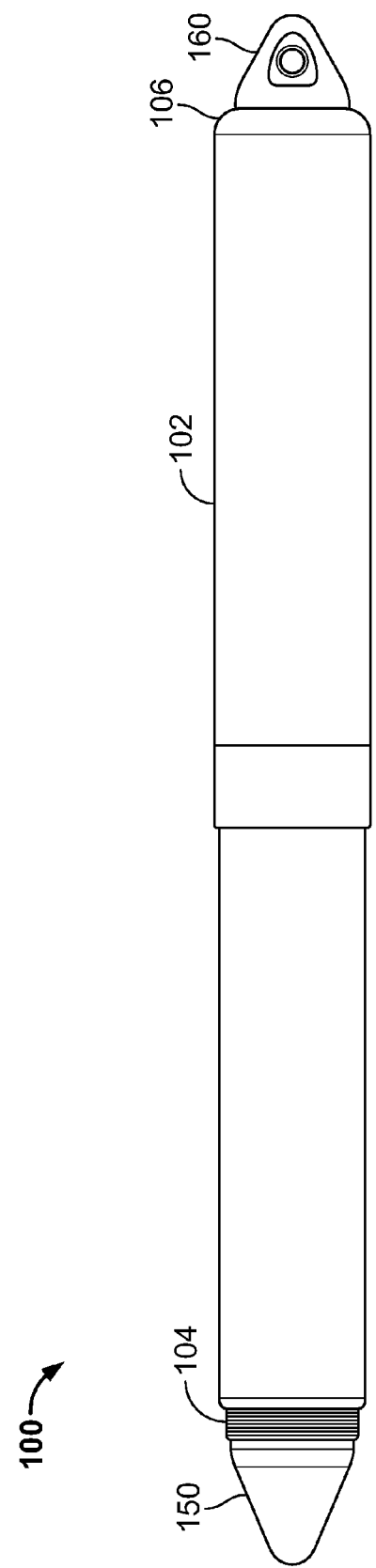
FIG. 1 is a side view of one embodiment of a microstimulator, according to the invention.
Figure 2:
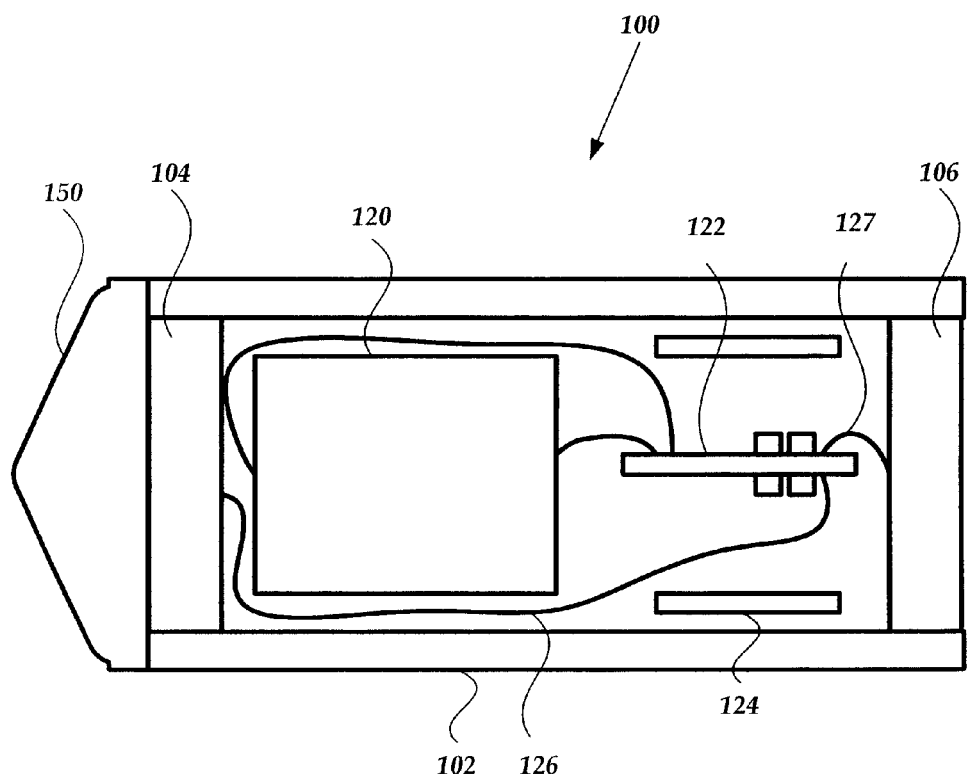
FIG. 2 is a cross-sectional view of one embodiment of a microstimulator, according to the invention.

FIG. 1 illustrates one embodiment of an implantable microstimulator 100. The implantable microstimulator 100 includes a housing 102, a dissecting tip 150, and an extraction aid 160. It will be recognized that a microstimulator may have only a dissecting tip or only an extraction aid or the microstimulator may have both. FIG. 2 illustrates internal components of one embodiment of a microstimulator 100. In this particular illustrated embodiment, the microstimulator includes a dissecting tip 150, but does not include an extraction aid. The microstimulator 100 of FIG. 2 includes a first electrode 104, a second electrode 106, a power source 120, an electronics subassembly 122, and an optional antenna 124. Other embodiments of an implantable microstimulator may include more or fewer components. It will be understood that the power source 120 and/or components of the electronics subassembly 122 and/or the optional antenna 124 can be provided outside of the housing in a separate unit and coupled to the implantable microstimulator by a lead. Examples of such arrangements are described in U.S. patent application Ser. No. 11/056,762, incorporated herein by reference.

The housing 102 can be formed of any material that resists the transport of moisture into the interior of the housing and is sufficiently sturdy to protect the components on the interior of the housing from damage under expected implantation and usage conditions. Suitable materials for the housing (or a portion of the housing) include metals, ceramics, and plastics. For example, the housing may include a ceramic portion brazed to a metal portion, where the metal portion, optionally, acts as an electrode as disclosed in, for example, U.S. Patent Application Publication No. 2004/0059392. As another example, the housing, or a portion of the housing, can be made of plastic, as disclosed in, for example, U.S. patent application Ser. No. 11/040,209.

The thickness of the walls of the housing may also impact the moisture permeability of the housing. A minimum thickness needed to achieve a particular degree of resistance to moisture transport will often depend on the material selected for the housing. In general, however, the thickness of the walls of the housing is at least 100 μm and typically ranges from 50 to 10,000 μm.

The housing can have any shape including, for example, cylindrical, conical, parallelepiped, cubic, and the like. In at least some embodiments, a cylindrical shape is preferred. The lateral cross-sectional dimensions can be the same or can vary along the length of the housing. In one embodiment, the housing has a cylindrical shape with a uniform diameter along the length of the housing. The uniform diameter can be, for example, no greater then 5 mm, no greater than 4 mm, no greater than 3.3 mm, or no greater than 3 mm. This uniform diameter can be in the range of, for example, 1 to 5 mm. In another embodiment, the housing is a cylinder that is wider at the ends and narrower in the middle or the housing is a cylinder that is wider in the middle and narrower at the ends.

The electrodes 104, 106 form the anode and cathode of the microstimulator. The one or more electrodes 104, 106 of the microstimulator unit can be formed using any conductive material including metals, alloys, and conductive polymers/plastics. Preferably, the electrodes are formed of material(s) that does not substantially corrode under the operating conditions and in the operating environment for the expected lifetime of the microstimulator unit. Examples of suitable materials include conductive materials such as, for example, titanium, iridium, platinum, platinum/iridium alloy, stainless steel, and the like.

The electrodes 104, 106 can be formed entirely of a single conductive material, such as a metal or alloy, or one or both of the electrodes can be formed using a combination of conductive materials such as, for example, a conductive coating over a bulk metallic electrode. As another example, one or both of the electrodes 104, 106 can be formed from a polymeric material that is at least partially, or fully, coated with a conductive coating, such as a metal, alloy, or conductive oxide (e.g., iridium oxide) coating.

In one embodiment, each of the one or more electrodes 104, 106 is a solid body that fits into or over one end of the housing 102. The electrode can be coupled to the battery and electronic subassembly 122 by attaching a conductor 126, 127 to a surface of the electrode. In one embodiment, one or both of the electrodes 104, 106 may be positioned at ends of the housing 102. In at least some embodiments, the electrodes 104, 106 are disposed at opposing or opposite ends of the housing 102. For example, the electrodes 104, 106 can be disposed at opposite ends of a cylindrical housing, as illustrated in FIGS. 1 and 2.

In at least some embodiments, the length of the combined housing 102 and electrodes 104, 106 is no greater than 30 mm. Typically the length of the combined housing 102 and electrodes 104, 106 is in the range of 10 to 30 mm.

The microstimulator 100 can include a dissecting tip 150, as illustrated in FIGS. 1 and 2. Preferably, the dissecting tip is a blunt dissecting tip. The dissecting tip can be formed of any suitable material including, metals and plastics. The dissecting tip may be conducting or non-conducting. The dissecting tip can have any shape suitable for dissecting the desired tissue. In one embodiment, the dissecting tip is cone-shaped with a blunt tip. The dissecting tip can be coupled to the housing (or another portion of the microstimulator, such as an electrode) using any method including, but not limited to, welding, brazing, adhesively mounting the dissecting tip to the housing, threading the dissecting tip onto the housing, or forming the dissecting tip with the housing (e.g., simultaneously molding the two parts together.)

The dissecting tip is typically disposed at one end of the housing. The dissecting tip can be disposed on an electrode 104 of the microstimulator, as illustrated in FIGS. 1 and 2, or the dissecting tip can be disposed on the end with the electrode or elsewhere on the housing. In some embodiments, a conductive (e.g., metal) dissecting tip 150 can act as the electrode 104 or can be in electrical communication with the electrode 104. In some embodiments, the dissecting tip can also be used as an electrode to locate the tissue to be stimulated. The electronic subassembly in the housing can be configured to provide pulses to assist in finding the tissue and may control or send data to an external control device to control the pulses. Alternatively, a separate electronic assembly may be coupled to the microstimulator or dissecting tip to assist in identifying the position of the microstimulator relative to the tissue to be stimulated when the dissecting tip 150 is conductive. In that case the dissecting tip 150 can function concurrently as an electrode 104. Alternatively, the surface of the tip can be entirely or partially coated by insulating materials to form an entirely non-conductive probing tip or a conductive probing tip with a desired stimulating surface pattern.

In one embodiment, the dissecting tip is a blunt dissecting tip formed of metal, such as titanium, platinum or iridium coating. The dissecting tip is coupled to an electrode by laser welding. The welding seam between the blunt dissecting tip and the electrode is covered, e.g., by silicone rubber or a biocompatible epoxy.

Additionally or alternatively, the microstimulator 100 can include an extraction aid 160. The extraction aid is typically coupled to one end of the microstimulator housing 102, although other configurations are possible. The extraction aid includes an arrangement that allows for the attachment of an extraction line. The extraction aid 160 can be, for example, an attachment with a hole to which the extraction line can be attached or through which the extraction line can be looped. However, it will be recognized that other arrangements, including more elaborate arrangements such as clamping mechanisms, can be used.

The extraction aid can be made out of any material including metal, alloys, and plastic. The extraction aid 160 can be disposed on an electrode 106 of the microstimulator or the extraction aid can be disposed on the end of the microstimulator and the electrode 106 can be disposed elsewhere on the housing. In some embodiments, a conductive (e.g., metal) extraction aid 160 can act as the electrode 106 or can be in electrical communication with the electrode 106. In other embodiments, the extraction aid is non-conducting and disposed over a portion of the electrode 106.

The extraction aid can be coupled to the housing (or another portion of the microstimulator, such as an electrode) using an method including, but not limited to, welding, brazing, adhesively mounting the extraction aid to the housing, threading the extraction aid on the housing, or forming the extraction aid with the housing (e.g., simultaneously molding the two parts together.)

Figure 3:
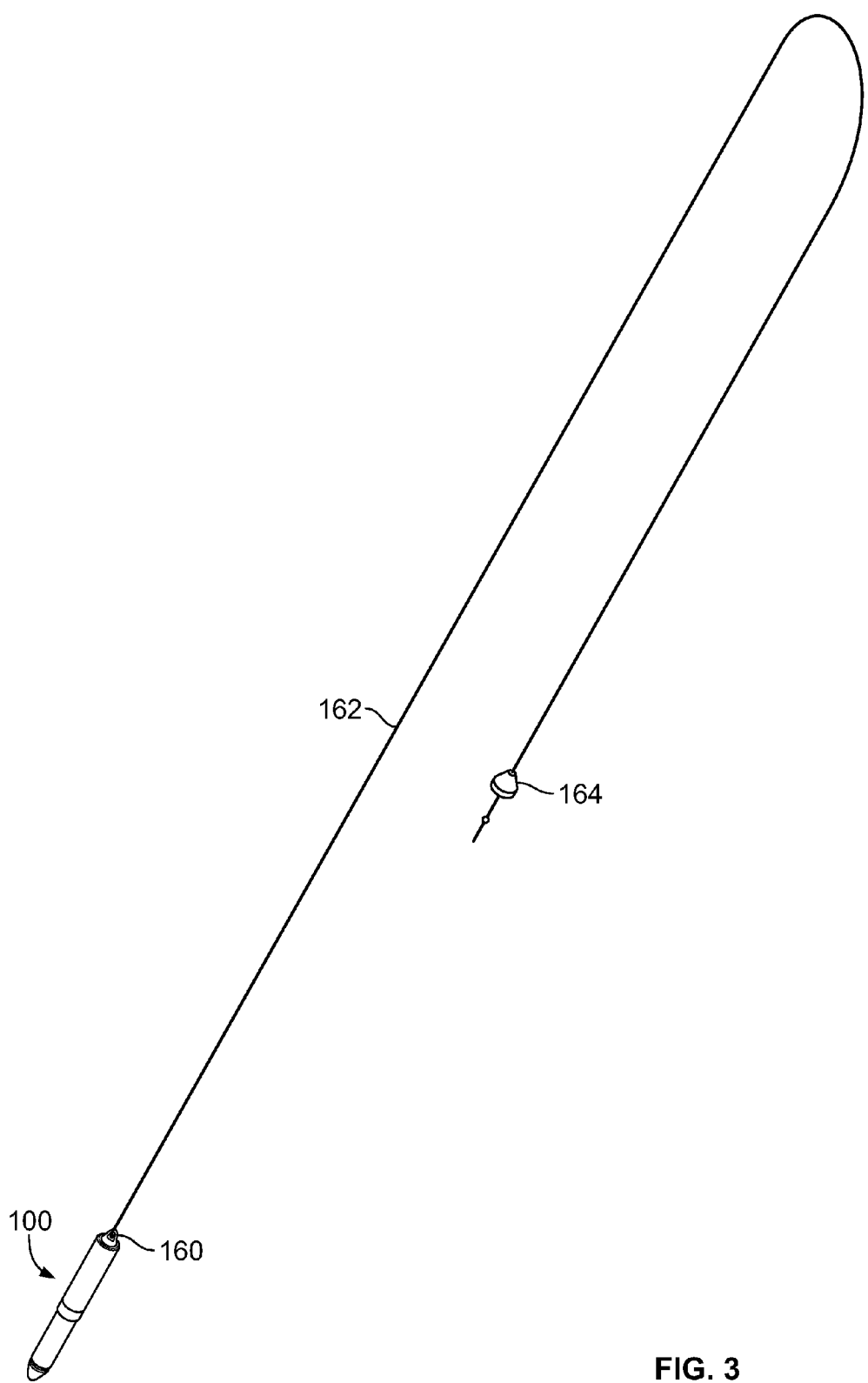
FIG. 3 is a perspective view of one embodiment of a microstimulator with an extraction line and an anchor, according to the invention.

FIG. 3 illustrates one embodiment of the microstimulator 100 with extraction aid 160, extraction line 162, and anchor 164. The extraction line 162 can be any suitable material, such as suture material, that can be implanted in the patient. Optionally, an anchor 164 can be attached to the extraction line 162. This anchor 164 can be implanted elsewhere in the patient and provides a method for finding the extraction line and retrieving the microstimulator. For example, the anchor can be implanted near the skin of the patient. The anchor can be made of a material (e.g., stainless steel) that is relatively easy to detect by x-ray or other detection methods so that the position of the anchor can be readily identified. When extraction of the microstimulator is desired, the anchor can be identified and an extraction tool can follow the extraction line to the microstimulator. The extraction line can be made with metal or non-metal, such as titanium, silk, Nylon, Teflon, polyester, and the like.

A power source 120 can be disposed within the housing 100. Any power source can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 124 or a secondary antenna. The external power source can be in a device that is mounted on the skin of the user or in a unit that is provided near the microstimulator user on a permanent or periodic basis.

If the power source 120 is a rechargeable battery, the battery may be recharged using the optional antenna 124, if desired. Power can be provided to the battery 120 for recharging by inductively coupling the battery through the antenna to a recharging unit 210 (see FIG. 5) external to the user. Examples of such arrangements can be found in the microstimulator references identified above.

Figure 4:
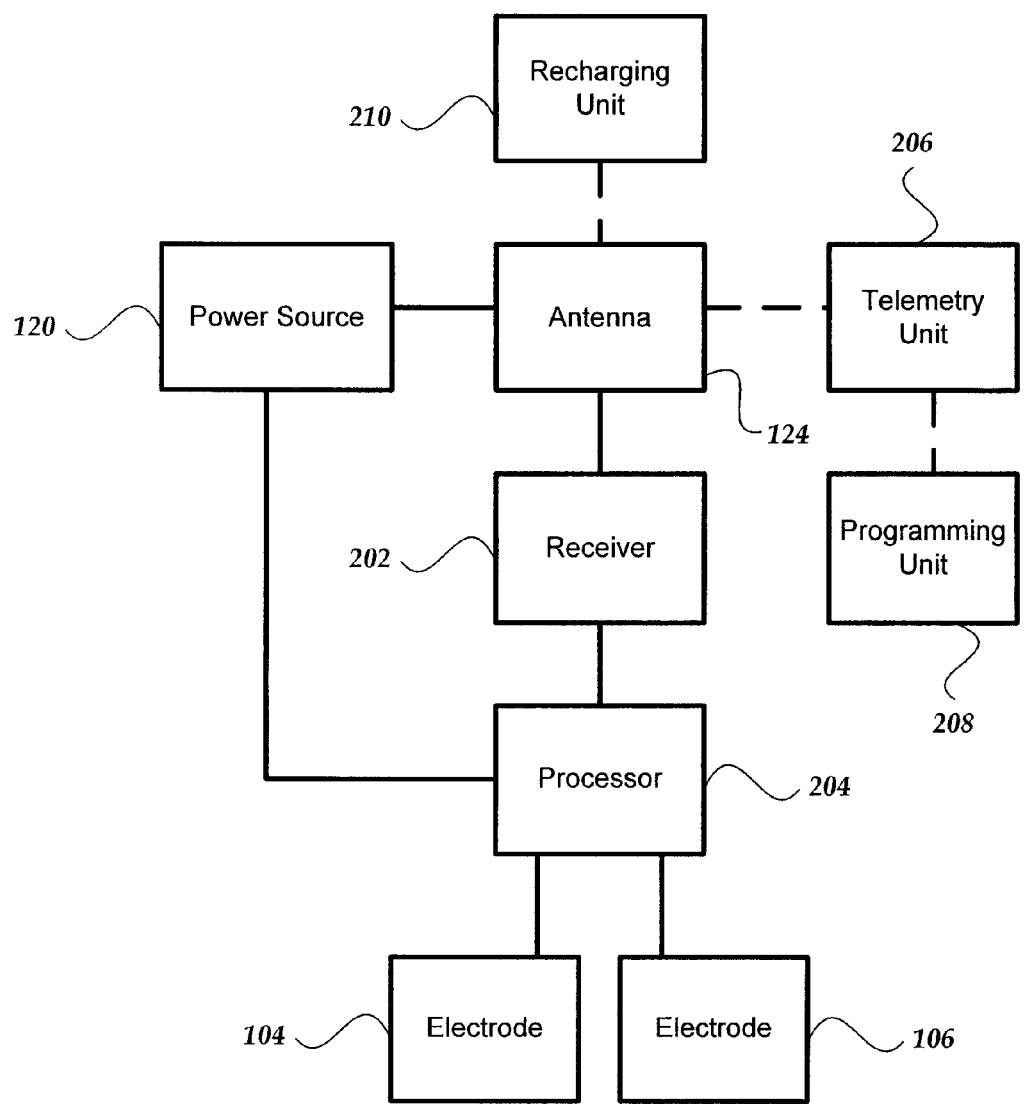
FIG. 4 is a schematic overview of components for an exemplary system for microstimulation of body tissues, according to the invention.

In one embodiment, electrical current is emitted by the electrodes 104, 106 to simulate motor nerve fibers, muscle fibers, or other body tissues near the microstimulator. The electronic subassembly 122 provides the electronics used to operate the microstimulator and generate the electrical pulses at the electrodes 104, 106 to produce stimulation of the body tissues. FIG. 4 illustrates one embodiment of components of the electronic subassembly and associated units. It will be understood that the electronic subassembly can include more, fewer, or different components and can have a variety of different configurations including those configurations disclosed in the microstimulator references cited above. Some or all of the components of the electronic subassembly can be positioned on one or more circuit boards or similar carriers within the housing, if desired.

In the illustrated embodiment, a processor 204 is provided to control the timing and electrical characteristics of the microstimulator. For example, the processor can, if desired, control one or more of the timing, frequency, strength, duration, and waveform of the pulses. Any processor can be used and can be as simple as an electronic device that produces pulses at a regular interval or the processor can be capable of receiving and interpreting instructions from an external programming unit 208 that allow modification of pulse characteristics. In the illustrated embodiment, the processor 204 is coupled to a receiver 202 which, in turn, is coupled to the optional antenna 124. This allows the processor to receive instructions from an external source to direct the pulse characteristics.

In one embodiment, the antenna 124 is capable of receiving signals (e.g., RF signals) from an external telemetry unit 206 which is programmed by a programming unit 208. The programming unit 208 can be external to, or part of, the telemetry unit 206. The telemetry unit 206 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the implanted microstimulator. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 124 and receiver 202 can be used to modify or otherwise direct the operation of the microstimulator. For example, the signals may be used to modify the pulses of the microstimulator such as modifying one or more of pulse duration, pulse frequency, pulse waveform, and pulse strength. The signals may also direct the microstimulator to cease operation or to start operation or to start charging the battery.

Optionally, the microstimulator may include a transmitter (not shown) coupled to the processor and antenna for transmitting signals back to the telemetry unit 206 or another unit capable of receiving the signals. For example, the microstimulator may transmit signals indicating whether the microstimulator is operating properly or not or indicating when the battery needs to be charged. The processor may also be capable of transmitting information about the pulse characteristics so that a user or clinician can determine or verify the characteristics.

The optional antenna 124 can have any form. In one embodiment, the antenna comprises a coiled wire that is wrapped at least partially around the electronic subassembly within or on the housing.

Any method of manufacture of the microstimulator can be used. For example, the electronic subassembly, power source, and antenna can be manufactured as described in U.S. Patent Application Publication No. 2004/0059392. These components can then be placed inside the housing. One or both of the electrodes can be formed with or attached to the housing with conductors from the electronic subassembly. Coatings on the electrodes or housing, if any, can be applied at appropriate points during the manufacturing process. The dissecting tip and the extraction aid can be attached to the microstimulator as described above.

The microstimulator can be implanted into the body tissue using a variety of methods including surgical methods. In some embodiments, the microstimulator can be implanted using a hypodermic needle or other insertion cannula. Examples of insertion techniques can be found in U.S. Pat. No. 6,051,017.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable microstimulator comprising:
   a housing having a first end;
   an electronic subassembly disposed within the housing;
   a plurality of electrodes disposed on the housing and coupled to the electronic subassembly; and
   a dissecting tip disposed at the first end of the housing, wherein the dissecting tip is dimensioned to open a path large enough through which the housing may be implanted into a body of a patient.

2. The implantable microstimulator of claim 1, wherein the dissecting tip is a blunt dissecting tip.

3. The implantable microstimulator of claim 1, wherein the dissecting tip is metal.

4. The implantable microstimulator of claim 2, wherein the blunt dissecting tip is in electrical communication with at least one of the plurality of electrodes.

5. The implantable microstimulator of claim 2, wherein the blunt dissecting tip is conical.

6. The implantable microstimulator of claim 1, wherein:
   the housing comprises a second end; and
   the implantable microstimulator further comprises an extraction aid disposed at the second end of the housing and configured and arranged for attachment of an extraction line.

7. The implantable microstimulator of claim 6, further comprising an extraction line coupled to the extraction aid.

8. The implantable microstimulator of claim 7, further comprising an anchor attached to the extraction line.

9. The implantable microstimulator of claim 6, wherein the extraction aid defines a hole through which an extraction line can be passed.

10. The implantable microstimulator of claim 1, wherein the housing comprises a sealed material configured to resist transport of moisture into an interior of the housing after implantation.

11. The implantable microstimulator of claim 1, wherein the dissecting tip comprises a cone-shaped member that is coupled to the first end of the housing by a weld, a braze, an adhesive, or a threaded surface.

12. The implantable microstimulator of claim 1, wherein the plurality of electrodes includes the dissecting tip and the dissecting tip is coupled to the electronic subassembly.

13. The implantable microstimulator of claim 1, further comprising:
   a battery disposed within the housing; and
   an electrical connection between the battery and the electronic subassembly.

14. The implantable microstimulator of claim 1, wherein the electronic subassembly comprises a programmable processor adapted to receive and interpret instructions from an external programming unit.

15. A method of using an implantable microstimulator, the method comprising:
   providing an implantable microstimulator comprising a housing having a first end, an electronic subassembly disposed within the housing, a plurality of electrodes disposed on the housing and coupled to the electronic subassembly, and a dissecting tip disposed at the first end of the housing, wherein the dissecting tip is dimensioned to open a path large enough through which the housing may be implanted into a body of a patient;
   inserting the microstimulator in a body of a patient using the dissecting tip to open a path to body tissue to be stimulated; and
   providing signals to the electrodes to stimulate the body tissue.

16. The method of claim 15, wherein:
   the dissecting tip is conductive and is in electrical communication with at least one of the plurality of electrodes; and
   providing signals to the electrodes comprises using the dissecting tip as an electrode to assist in stimulating the body tissue.

17. The method of claim 15, wherein the microstimulator further comprises an extraction aid disposed on a second end of the housing, the method further comprising attaching an extraction line to the extraction aid.

18. The method of claim 17, further comprising attaching an anchor to the extraction line.

19. The method of claim 18, further comprising implanting the anchor near a skin region of the patient.

20. The method of claim 18, further comprising identifying the anchor prior to extracting the microstimulator.

21. The method of claim 17, further comprising extracting the microstimulator using the extraction line.

22. The method of claim 15, wherein providing the signals to the electrodes comprises:

receiving and interpreting instructions from an external programming unit; and modifying a characteristic of a signal provided to the electrodes based on the instructions from the external programming unit.

23. The method of claim 15, further comprising finding, as the microstimulator is implanted, a tissue to be stimulated by providing a signal to the dissecting tip.

24. A device comprising:

an implantable microstimulator comprising:

an elongate housing comprising a material that prevents a transport of moisture into an interior of the housing, the housing having a front end;

an electronic subassembly housed within the housing, the electronic subassembly configured to generate electrical pulses for stimulation of tissue;

a first electrode mounted to the housing and coupled to the electronic subassembly to receive the electrical pulses for the stimulation of tissue; and a dissecting tip mounted to the front end of the elongate housing, wherein the dissecting tip is dimensioned to open a path large enough through which the elongate housing may be implanted into a body of a patient.

25. The device of claim 24, wherein the dissecting tip is dimensioned to substantially cover the entire lateral sectional area of the elongate housing.

* * * * *